United States Patent
Guttman et al.

(10) Patent No.: US 10,247,745 B2
(45) Date of Patent: Apr. 2, 2019

(54) GLYCAN SAMPLE PREPARATION

(71) Applicant: Beckman Coulter, Inc., Brea, CA (US)

(72) Inventors: Andras Guttman, San Diego, CA (US); Clarence Lew, Irvine, CA (US); Marton Szigeti, Budapest (HU); Csaba Varadi, Karcsa (HU)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 15/307,113

(22) PCT Filed: Apr. 27, 2015

(86) PCT No.: PCT/IB2015/053052
§ 371 (c)(1),
(2) Date: Oct. 27, 2016

(87) PCT Pub. No.: WO2015/166399
PCT Pub. Date: Nov. 5, 2015

(65) Prior Publication Data
US 2017/0045538 A1    Feb. 16, 2017

Related U.S. Application Data

(60) Provisional application No. 62/150,722, filed on Apr. 21, 2015, provisional application No. 61/986,736, filed on Apr. 30, 2014.

(51) Int. Cl.
*G01N 35/00* (2006.01)
*C08B 37/00* (2006.01)
*B03C 1/02* (2006.01)
*B03C 5/00* (2006.01)

(52) U.S. Cl.
CPC ..... *G01N 35/0098* (2013.01); *C08B 37/0003* (2013.01); *G01N 35/0099* (2013.01); *G01N 2035/00356* (2013.01); *G01N 2400/12* (2013.01); *G01N 2400/38* (2013.01)

(58) Field of Classification Search
None
See application file for complete search history.

(56) References Cited

U.S. PATENT DOCUMENTS

| 2006/0120961 A1 | 6/2006 | Schneider et al. |
| 2011/0117601 A1* | 5/2011 | Haberger .......... C07K 16/2866 435/69.6 |
| 2011/0136727 A1 | 6/2011 | Svarovsky |
| 2013/0171658 A1 | 7/2013 | Fulton et al. |

FOREIGN PATENT DOCUMENTS

| EP | 1578519 B1 | 12/2012 | |
| WO | WO-2012037407 A1 * | 3/2012 | ............. C08B 37/00 |
| WO | 2012170491 A1 | 12/2012 | |

OTHER PUBLICATIONS

Sparbier, K. et al. 2005. Selective isolation of glycoproteins and glycopeptides for MALDI-TOF MS detection supported by magnetic particles. Journal of Biomolecular Techniques 16: 407-413. specif. pp. 407, 408, 413.*
Ruhaak, L.R. et al. 2010. Glycan labeling strategies and their use in identification and quantification. Analytical and Bioanalytical Chemistry 397: 3457-3481. specif. pp. 3457, 3459, 3460, 3463, 3468, 3477.*
International Search Report and Written Opinion for PCT/IB2015/053052 dated Jul. 29, 2015.
Glyco Kit MB-CovAC-Boronic—Instructions for Use, Bruker Daltonics, Revision 1, Jan. 2012, Copyright 2012 Bruker Daltonik GmbH.

* cited by examiner

*Primary Examiner* — Renee Claytor
*Assistant Examiner* — Sharon M Papciak

(57) ABSTRACT

The present teachings relate to methods, systems, and kits for the preparation, purification and/or analysis of a glycan or glycoconjugate, and specifically to a magnetic bead based sample preparation protocol that can enable full automation and reduced sample preparation time relative to current methods of glycoanalysis. In some aspects, the sample preparation protocol can provide for glycoconjugate capture, glycan release, fluorescent derivatization, and glycan purification for subsequent capillary electrophoresis, liquid chromatography, or other glycoanalytical method without requiring time-consuming sample preparation steps such as centrifugation or vacuum-centrifugation.

15 Claims, 8 Drawing Sheets

Average fluorescent intensity of detected peaks as a function of PNGase F digestion time at 37°C and 50°C incubation temperature.

Optimization of fluorophore glycan labeling conditions

CE-LIF based fluorescent intensity values with APTS labeling at 37°C and 50°C.

Magnetic Bead based N-glycan sample preparation
*4 hours, no centrifugation/no speedvac*

In solution PNGase F digestion: 50 °C for 1 hour (NEB kit)
Make the total volume up to 87.5 % acetonitrile concentration and capture the glycans by 200 µL magnetic bead suspension (Agencourt Clenseq),
Elution by 21 µL of 40 mM APTS solution in 20% acetic acid

In solution labeling by the addition of 7 µL of 1 M NaCNB$_3$ in THF
Incubation at 37 °C for 2 hours

Sample clean-up
Add acetonitrile solution to get 87.5 % final concentration and remove the supernatant
Washing step: Add 150 µL of 87.5 % acetonitrile to the sample and mix with the beads
(3x)
Elution step: 25 µL of HPLC water

CE-LIF Analysis

Figure 8

GLYCAN SAMPLE PREPARATION

RELATED APPLICATIONS

This application claims the benefit of priority from U.S. Provisional Applications No. 61/986,736 filed on Apr. 30, 2014 and 62/150,722, filed on Apr. 21, 2015, the contents of both of which are hereby incorporated by reference in their entirety.

FIELD

Methods, systems, and kits for the analysis of glycans and/or glycoconjugates are disclosed herein. In some aspects, the present teachings can enable automated glycoanalysis protocols that exhibit a substantially reduced sample preparation time relative to known methods.

INTRODUCTION

Protein glycosylation typically refers to a post-translational modification in which an oligosaccharide or glycan is attached to a protein. Given the importance of glycosylation on protein folding, transport, and cell-cell interactions, for example, many research tools have been developed to characterize and/or analyze glycoconjugates and the glycans associated therewith. Such tools have become critical in the biomedical sciences, biopharmaceutical industry (e.g., biomarker discovery), and in efficacy/safety assessment of protein therapeutics for regulatory agencies.

Though the most common glycoanalytical methods of capillary electrophoresis and hydrophilic interaction liquid chromatography can be effective, these methods can necessitate extensive sample preparation, including glycoprotein capture, N-glycan release, fluorescent derivatization, purification, and pre-concentration steps. Currently used protocols to fulfill these tasks, however, are time consuming and require multiple centrifugation and/or vacuum-centrifugation steps, for example, thereby reducing throughput and making automation difficult and/or expensive.

Accordingly, there remains a need for efficient and effective methods for the purification of glycans and/or the analysis of glycoconjugates or the glycans associated therewith.

SUMMARY

The present teachings relate to methods, systems, and kits for the purification and/or analysis of a glycoconjugate or glycan, and specifically, to magnetic bead-based sample preparation methods that can enable full automation and/or reduced sample preparation time relative to current protocols. In some aspects, the methods described herein can provide for one or more of glycoprotein digestion, N-glycan release, fluorescent labeling, and glycan purification for subsequent capillary electrophoresis with laser induced fluorescence detection (CE-LIF), liquid chromatography (LC), or other analytical methods (e.g., mass spectrometry (MS), nuclear magnetic resonance (NMR)), without requiring time-consuming sample preparation steps such as centrifugation or vacuum-centrifugation.

In accordance with various aspects, certain embodiments of the applicants' teachings relate to a method of purifying glycans that comprises reacting a sample containing one or more glycoconjugates (e.g., glycoproteins, glycopeptides, antibodies, proteoglycan, glycosphingolipid, chondroitin sulfate, heparin sulfate, hyaluronan, glycolipid, glycoseaminoglycan, fusion glycoprotein, antibody-drug conjugate) with a deglycosylation reagent (e.g., an endoglycosidase for N-linked glycans, beta elimination for O-linked glycans) so as to release glycans from the glycoconjugates, associating the released glycans with a plurality of magnetic particles (e.g., carboxyl-coated magnetic beads), applying a magnetic field to draw down the plurality of magnetic particles having the released glycans associated therewith, removing a supernatant from the drawn-down magnetic particles so as to remove the deglycosylation reagent (e.g., enzyme) and the deglycosylated sample, and dissociating or eluting the glycans from the magnetic particles. In some aspects, the method can prepare the glycans for analysis via one of CE (e.g., with LIF, with UV labeling), LC (e.g., with fluorescent or UV detection), MS, and NMR, and combinations thereof. In some aspects, the glycans are purified without a centrifugation or vacuum centrifugation step.

In accordance with various aspects, certain embodiments of the applicants' teachings relate to a method of analyzing one or more glycoconjugates (e.g., glycoproteins, glycopeptides, antibodies, proteoglycan, glycosphingolipid, chondroitin sulfate, heparin sulfate, hyaluronan, glycolipid, glycoseaminoglycan, fusion glycoprotein, antibody-drug conjugate) that comprises reacting a sample containing one or more glycoconjugates with a deglycosylation reagent (e.g., an endoglycosidase) to release glycans from the glycoconjugates and associating the glycans with a plurality of magnetic particles (e.g., carboxyl-coated magnetic beads). A magnetic field can be applied to draw down the plurality of magnetic particles having the glycans associated therewith, and the supernatant can be removed so as to remove the deglycosylation enzyme and deglycosylated conjugates from the drawn-down magnetic particles. The glycans can be reacted with a labeling reagent so as to form labeled glycans that can then be analyzed (e.g., via capillary electrophoresis with laser induced fluorescent or UV detection). In accordance with various aspects of the present teachings, the labeled glycans can be prepared for analysis without centrifugation or vacuum centrifugation.

The method can include eluting the glycans from the magnetic particles before or after labeling the glycans. In some aspects, for example, the method can include eluting the glycans from the magnetic particles prior to reacting the glycans with the labeling reagent. For example, the glycans can be eluted from the magnetic particles by adding a mixture comprising the labeling reagent and an acid catalyst (e.g., acetic acid). In related aspects, the glycans can be reacted with the labeling reagent so as to form labeled glycans by adding a reducing agent (e.g., NaBH$_3$CN or pic-BH3) to initiate the reaction of the glycans with the labeling reagent.

In some aspects, the method can also comprise associating the labeled glycans with the plurality of magnetic particles (e.g., magnetic microparticles, beads), applying a magnetic field to draw down the plurality of magnetic particles having the labeled glycans associated therewith, removing a supernatant from the drawn-down plurality of magnetic particles having the labeled glycans associated therewith so to remove excess labeling reagent, and eluting the labeled glycans from the plurality of magnetic particles. For example, the labeled glycans can be associated with the plurality of magnetic particles by adding acetonitrile and the labeled glycans can be eluted from the plurality of magnetic beads by adding an aqueous media (e.g., water).

In accordance with various aspects of the present teachings, the deglycolsylation reagent can comprise PNGase F enzyme, glycans can be associated with the plurality of magnetic particles by adding acetonitrile, and the labeling reagent can comprise one of 1-aminopyrene-3,6,8-trisulfonic acid (APTS), 8-aminonaphthalene-1,3,6-trisulfonic acid (ANTS), 2-anthranilic acid (2-AA), 2-aminobenzoic acid (2-AB) (that can be reacted with the glycans, for example, by adding a reducing agent such as $NaBH_3CN$ or pic-BH3).

In accordance with various aspects, certain embodiments of the applicants' teachings relate to a kit for purifying glycans that can comprise a plurality of carboxyl-coated magnetic particles, deglycosylation reagents for releasing glycans from glycoconjugates contained within a sample (e.g., one or more endoglycosidases, PNGase F, hydrazine), and reagents for associating the glycans with the plurality of carboxyl-coated magnetic particles.

In some aspects, the kit can further comprise reagents for labeling of the released glycans, particularly for fluorescent labeling of the released glycans. For example, the kits can include one or more of APTS, ANTS, 2-AA, 2-AB, an acid catalyst (e.g., acetic acid), and a reducing agent such as $NaBH_3CN$ or pic-BH3.

In some aspects, reagents for associating the released glycans with the plurality of carboxyl-coated magnetic particles comprises acetonitrile.

In some aspects, the method can further comprise maintaining a temperature equal to or greater than about 37° C. (e.g., equal to or greater than about 50° C.) when reacting the sample with the deglycosylation enzyme.

In various aspects, the kit can further comprise reagents for analyzing the labeled glycans via capillary electrophoresis (e.g., with laser induced fluorescent detection), liquid chromatography, MS, or NMR. For example, the kit can include a fluorescently-labeled internal standard for the CE-LIF analysis of the labeled glycans (e.g., APTS-, ANTS-, 2-AA-, or 2-AB-labeled maltose).

In accordance with various aspects, a composition for separating glycans using capillary electrophoresis is provided comprising lithium acetate buffer, polyethylene oxide, ethylene glycol and linear polyacrylamide.

In various embodiments, the lithium acetate is at a concentration in the composition of between 10 mM and 50 mM at a pH of between 4 and 5.5, the polyethylene oxide has a molecular weight of between 100 and 1000 kDa and is at a concentration in the composition of between 0.5% and 5%, the ethylene glycol is at a concentration in the composition of less than 60% and/or the linear polyacrylamide has a molecular weight of about 10 kDa and is at a concentration in the composition of between 0.5% and 5%.

In various embodiments, the composition can comprise lithium acetate buffer at a concentration in the composition of between 25 and 30 mM at a pH of about 4.75; polyethylene oxide having a molecular weight of about 900 kDa at a concentration in the composition of about 1%; ethylene glycol at a concentration in the composition of about 20%; linear polyacrylamide having a molecular weight of about 10 kDa at a concentration in the composition of about 3%.

These and other features of the applicants' teachings are set forth herein.

BRIEF DESCRIPTION OF THE DRAWINGS

The skilled person in the art will understand that the drawings, described below, are for illustration purposes only. The drawings are not intended to limit the scope of the applicants' teachings in any way.

FIG. 8 schematically depicts an exemplary magnetic bead based sample preparation workflow for N-glycosylation analysis in accordance with various aspects of the present teachings.

DETAILED DESCRIPTION

Figure 1:
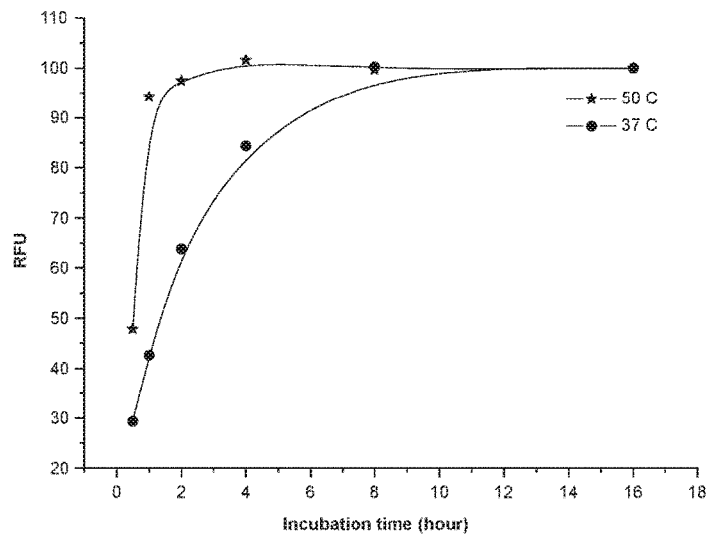
FIG. 1 illustrates the effect of incubation duration and temperatures during PNGase F digestion in accordance with various aspects of the applicants' teachings.

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

In accordance with various aspects of the present teachings, the methods, systems, and kits described herein can be used in the purification and/or analysis of a glycoconjugate or glycan that can enable full automation and/or reduce sample preparation time relative to current protocols. In some aspects, the methods described herein can provide for one or more of glycoconjugate digestion and/or glycan release, fluorescent labeling, and glycan purification for subsequent analysis, without requiring time-consuming sample preparation steps such as centrifugation or vacuum-centrifugation. Full automation to enable high throughput glycosylation profiling and sequencing, for example, may be vital to fulfill contemporary needs of the biopharmaceutical industry (e.g., development of biotherapeutic agents, biomarker discovery), and in regulatory agencies' efficacy/safety assessments of protein therapeutics, which require high-throughput and highly reproducible glycosylation screening methods. Despite this need, one of the major handicaps of currently used sample preparation protocols for glycosylation analysis is the lack of easy automation, which currently require high end (expensive) robotic systems with centrifugation capabilities.

In accordance with various aspects, the exemplary magnetic bead-based sample preparation described herein can be performed in several hours, without requiring any centrifugation and/or vacuum centrifugation steps, thus enabling rapid, fully-automatable analysis that can utilize, for example, shorter incubation times during glycan release and labeling, the use of liquid handling robots for sample preparation, and/or multicapillary methods. As described below, the exemplary methods can thus improve processing time, efficiency, reproducibility, and ease of automation relative to conventional centrifugation-based sample preparation protocols.

In one embodiment, for example, an exemplary method generally comprises the following five individual steps, though it will be appreciated that methods that include more or fewer steps are within the scope of the present teachings: 1) deglycosylation of the gluconjugate; 2) glycan capture; 3) glycan labeling; 4) clean up; and 5) glycan analysis (e.g., by CE, LC, MS, NMR).

It will further be appreciated that any sample containing or suspected of containing a glycan or glycoconjugate can be used in accordance with the present teachings, including a sample of blood, plasma, serum, urine or saliva. Further, the sample can contain free glycans (e.g., a previously deglycosylated sample) and/or glycoconjugates.

Exemplary glycoconjugates that can be analyzed according to the present teachings include glycoproteins such as fetuin, RNase B, and antibodies (e.g., IgG), all by way of non-limiting example. Other exemplary glycoconjugates that can be utilized include proteoglycan, glycosphingolipid, chondroitin sulfate, heparin sulfate, hyaluronan, glycolipid, glycoseaminoglycan, fusion glycoprotein, and antibody-drug conjugates. The glycans that are associated with the glycoconjugates generally comprise one or more sugar units (e.g., glucose, fucose, mannose, xylose, sialic acids N-Acetylglucosamine (GlcNAc), N-acetylgalactosamine (GalNAc) and oligosaccharides) that are covalently bonded to the base molecule via a glycosidic bond, for example. As will be appreciated by a person skilled in the art, the glycans can comprise a variety of carbohydrate units, branched or unbranched chains with various linkages and positions, and/or oligosaccharides of various lengths that can be attached to the base molecule via N-linked glycosylation (e.g., a glycan linked to an amide nitrogen of an asparagine (Asn) residue of a protein), O-linked glycosylation (e.g., a glycan linked to an oxygen atom of amino acid residue in a protein such as O-GalNAc or O-GlcNAc), C-linked glycosylation (e.g., mannose added to a tryptophan residue in an amino acid sequence), and phospho-serine glycosylation (e.g., a glycan linked through the phosphate in a phospho-serine), all by way of non-limiting example.

Deglycosylation

In some aspects, methods of analyzing a glycoconjugate or glycan associated therewith can include a deglycosylation step that breaks the glycosidic bond so as to remove the glycan from the glycoconjugate. It will be appreciated that any deglycosylation reagent known in the art and modified in accordance with the present teachings can be utilized. By way of non-limiting example, methods and systems in accordance with the present teachings can utilize PNGase F (e.g., to remove N-linked oligosaccharides from the glycoproteins), PNGase A, other endoglycosidases such as O-Glycosidase, Endoglycosidase H and the Endoglycosidase F), and exoglycosidases (e.g., Neuraminidase), chemical agents such as hydrazine and mixtures thereof.

As discussed in detail below, though PNGase F is conventionally used in enzymatic deglycosylations of N-glycans at 37° C. with overnight incubation due to its stability, specificity and simple sample preparation conditions, applicants have achieved significantly reduced deglycosylation times by performing the deglycosylation at elevated temperatures (e.g., greater than 37° C., about 50° C.). Indeed, maximum peak intensities of the released glycans were found to occur after one hour of incubation time at 50° C., whereas the N-deglycosylation process proceeded significantly slower at the conventional 37° C.

It should be appreciated in light of the present teachings that the methods of analyzing glycans can also be performed on a sample that has previously been deglycosylated (e.g., a sample containing glycans already dissociated from a protein or other biopolymer) or a sample containing only glycans (e.g., a glycan standard) such that a deglycosylation or digestion step is not required.

Glycan Capture

After the glycoconjugate has been digested such that at least a portion of the glycans are released therefrom, the released glycans can be separated from the deglycosylation reagent (e.g., enzyme) and any disassociated polypeptide, for example. In accordance with various aspects of the present teachings, for example, a suspension of magnetic particles can be mixed with the sample such that the glycans can become associated with the magnetic beads. In some aspects, the suspension of magnetic particles can comprise acetonitrile, which can promote the capture of the released glycans. Following the association, a magnetic field can be applied to the mixture so as to attract (e.g., draw down, separate) the magnetic particles having the glycans associated therewith such that the supernatant containing the non-associated deglycosylation reagent, such as an enzyme and remaining polypeptide can be removed, for example, by pouring off or aspirating the supernatant.

Applicants have surprisingly discovered that the carboxylate-modified surface of a polymeric-coated magnetic particle (e.g., a carboxyl-coated magnetic bead) can be particularly effective in capturing the released glycans or glycoconjugates. Though it was commonly believed that the negatively-charged carboxyl groups extending from the surface of a magnetic bead and negatively-charged glycans (e.g., syalilated) would repel one another and prevent glycan capture, the applicants' have found that the carboxyl-coated magnetic beads can effectively and efficiently lead to partitioning of charged and/or uncharged glycan. Such a result is counterintuitive, especially in light of the relatively small molecular weight of most glycans (i.e., such that the glycans should be more susceptible to repulsive forces). Without being bound by a particular theory, it is believed that the binding buffer (e.g., acetonitrile) acts as a crowding reagent around the carboxylated bead so as to form an environment favorable for glycan capture. Though to the applicants' knowledge the application of magnetic bead technology to the separation of glycans in accordance with the present teachings has not been performed, a commercial example of such a carboxyl-coated magnetic bead for use in accordance with the present teachings comprise Agencourt Cleanseq magnetic beads from Beckman Coulter, Inc. (Brea, Calif., USA).

Glycan Labeling

Some glycoanalytical methods require that the glycan(s) be labeled to enable further analysis and/or detection. By way of example, analysis of the glycans using CE-LIF can utilize chemical derivatization of the sugars in order to provide them with adequate charge and UV active or fluorescent characteristics. Accordingly, in some aspects, a glycan labeling step can be performed. In some aspects, the glycan can be labeled via a reductive amination based reaction, e.g., using one of 1-aminopyrene-3,6,8-trisulfonic acid (APTS), 8-aminonaphthalene-1,3,6-trisulfonic acid (ANTS), 2-anthranilic acid (2-AA), 2-aminobenzoic acid (2-AB), using one or more reducing agents, catalysts, and amounts of dye, all by way of non-limiting example. Exemplary reducing agents for initiating the reaction with the labeling reagent include sodium-cyanoborohydride ($NaBH_3CN$) and 2-picoline-borane (pic-BH3) or other reducing agents. In some aspects, the reducing agents or the use of the same can be optimized to reduce sialic acid loss. It will also be appreciated that various dye concentrations can be used so as to increase labeling efficiency, though more efficient clean-up steps may also be required to ensure excess dye removal.

Applicants have found that the labeling reaction with the glycans can occur while the glycans are associated with the magnetic particles or, for example, after being dissociated (e.g., eluted) from the magnetic particles. For example, in some aspects, the labeling reagent can be added to the magnetic particles with acetic acid, which can be effective to elute the glycans from their association with the magnetic particles. Following elution, the reducing agent can then be added to initiate the reaction of the labeling reagent (e.g., dye) with the glycans.

Clean-Up and Glycan Analysis

In some aspects, after the glycans have been labeled, excess labeling reagents (e.g., unconjugated APTS) can be removed via one or more clean-up steps. As discussed above, for example, free labeled glycans can be associated with the magnetic beads via the addition of acetonitrile. Following the association, a magnetic field can be applied to the mixture so as to attract the magnetic particles having the labeled glycans associated therewith such that the supernatant containing the excess labeling reagents can be removed, for example, by pouring off or aspirating the supernatant. In some aspects, acetonitrile can be added one or more times to wash the magnetic beads and labeled glycans associated therewith.

With the excess labeling agent removed, the labeled glycans can be released from the magnetic beads (e.g., through the addition of an eluent such as water). Though various volumes of the reagents for associating and releasing the glycans from the magnetic particles can be utilized to fully purify the labeled glycans, it will be appreciated that the degree of purification and sample loss may be inversely related such that the amount of the eluent necessary for obtaining adequate purification can be optimized to minimize possible sample loss.

Following addition of the eluent to release the labeled glycans from the magnetic particles, a magnetic field can again be applied to separate the magnetic particles from the eluate containing the free labeled glycans. The eluate (e.g., the supernatant relative to the drawn-down magnetic particles) can then be removed for further analysis, for example, via one of CE-LIF, LC, MS, and NMR.

When analyzing using Capillary Electrophoresis based analysis (e.g. CE-LIF), separation in CE of the glycans can be performed using gel compositions suitable for separation of the glycans. A suitable gel composition can include, for example, the use of lithium acetate buffer at concentrations in of approximately 10 mM-50 mM where the buffer is at a pH of between approximately 4 and 5.5. The composition further comprises polyethylene oxide at $M_v$ of between approximately 100 kDa and 1000 kDa at concentrations of between approximately 0.5% and 5%. The composition may also include ethylene glycol at a concentration of less than approximately 60%. The composition may also contain linear polyacrylamide (LPA) with molecular weight of about 10 kDa and at concentration of between 0.5% and 5%.

Preferably, the composition can comprise lithium acetate buffer with concentration between 25 and 30 mM, at pH of about 4.75, polyethylene oxide ($M_v$ of about 900 kDa) at concentration of 1%, ethylene glycol at concentration of about 20% and linear polyacrylamide (MW of about 10 kDa) at concentration of about 3%. Particularly preferred, the lithium acetate concentration in the composition is about 30 mM.

EXAMPLES

The above teachings will now be demonstrated using the following examples, provided to demonstrate but not limit the present teachings. As described below, an exemplary rapid and high-throughput magnetic bead based sample preparation workflow for CE-LIF based N-glycosylation analysis is provided in which all preparation steps can be easily automated using simple liquid handling robots. It is noted that in the exemplary workflows described below, centrifugation steps and overnight incubations, which are otherwise part of conventional glycan preparation methods, are avoided.

The exemplary sample preparation protocols have been demonstrated using representative glycoprotein standards with complex, sialylated and high mannose type glycosylations. As discussed below, all individual preparation steps, such as glycan release, fluorescent labeling and APTS-clean-up were optimized to decrease processing time and efficiency for the magnetic bead based method. It should be appreciated by those skilled in the art that adjustments can be made to the volumes, concentrations, and times described below, for example, to obtain optimum results in accordance with the present teachings.

Chemicals

Water and acetonitrile were Chromasolv HPLC grade. IgG, fetuin, RNase B, human serum, acetic acid, sodium-cyanoborohydride ($NaBH_3CN$), 2-picoline-borane (pic-BH3) were obtained from Sigma Aldrich (St. Louis, Mo.). 1-aminopyrene-3,6,8-trisulfonate (APTS), carbohydrate separation gel (NCHO), maltooligosaccharide ladder, and Agencourt Cleanseq magnetic beads were from Beckman Coulter, Inc. (Brea, Calif., USA). The deglycosylation kit (10 µL glycoprotein solution, 1 µL 10× denaturation buffer, 8 µL water, 2.5 µL 10× G7 buffer, 2.5 µL 10% NP40, 1 µL PNGase F) was purchased from New England Biolabs (Ipswich, Mass.).

Capillary Electrophoresis

Capillary electrophoresis profiling of APTS labeled N-glycans was performed in a PA800+ automated CE instrument (Beckman Coulter sold through Sciex), equipped with a solid state laser induced fluorescent detector (excitation 488 nm, emission 520 nm). All separations were accomplished in 50 cm effective length (60 cm total) neutral coated, 50 μm i.d. capillary columns filled with N—CHO Carbohydrate Separation Gel Buffer (both from Sciex). The applied electric field strength was 500 V/cm, with the cathode at the injection side and the anode at the detection side (reversed polarity). Samples were injected by pressure at 1 psi (6.89 kPa) for 5 seconds. For migration time correction and quantification purposes, APTS labeled maltose (G2) was co-injected with each sample as an internal standard. The Karat 32 version 9.1 software package (Sciex) was used for data acquisition and analysis.

Example 1

Optimization of the Incubation Time for Glycan Release

Utilizing a liquid handling robot-friendly open 96 well-plate format, the effect of temperature on the deglycosylation of a glycoconjugate was analyzed. As evaporation at temperatures greater than 60° C. could cause protein precipitation or buffer evaporation (especially in small volumes (e.g., 10-50 μL)), digestion efficiency was compared at 50° C. and 37° C. for the deglycosylation of IgG and fetuin glycoprotein standards using 0.5, 1, 2, 4, 8 and 16 hours of incubation. Each digestion reaction time-point mixture contained 7.7 mU PNGase F and was prepared following the manufacturer's protocol. Three releases were made with each digestion strategy and three repetitions were made with each release, generating nine data points per digestion time and temperature. The released glycans were APTS labeled and analyzed by CE-LIF.

Though no significant differences in peak distribution (as measured by peak area percentages) were observed between the two incubation strategies, the RFU values demonstrated changes in the amount of the released glycans. With reference now to FIG. 1, peak intensities at 37° C. increased significantly more slowly relative to 50° C., where the maximum level was reached after about one hour of incubation time. The similarity in area percentages compared to the overnight digestion suggest that the same glycosylation pattern can be released using shorter incubations (no digestion bias), with the main difference in the amount of released sugars. The higher temperature glycan release accelerated the reaction, and thus, PNGase F digestion was performed for one hour at 50° C. in the following steps.

APTS Labeling Optimization

Conditions for labeling so as to achieve the labeling efficiency of conventional centrifugation-based methods with respect to peak intensity and area distribution, while nonetheless accommodating simple liquid handling robots and magnetic bead based automation, were analyzed. In accordance with various aspects of the present teachings, high labeling efficiency was achieved without overnight incubation and vacuum-centrifugation based sample concentration.

First, mono- and bi-sialo glycan standards of A2G2S2, A2G2S1, FA2G2S2 and FA2G2S1 were labeled in duplicates with 20 mM APTS in 15% acetic acid for 2 hours at 37, 50, 65, and 80° C. Non-sialylated counterparts of these glycans (A2G2 and FA2G2) were also labeled and used for spiking the higher temperature reaction mixtures to identify possible temperature induced desialylation. As shown in FIG. 2A, the increase in the reaction temperature significantly elevated the desialylation process for all sialylated glycan standards. Bi-sialylated standards exhibited greater sialic acid loss. On average, 2% sialic acid loss was observed at 50° C., 11% at 65° C., and 33% at 80° C., suggesting that carefully chosen derivatization temperature can be important during glycan labeling when sialylated structures are expected in the sample.

The effect of incubation time was also examined at 37° C., with some differences observed between the overnight incubation and the two hour incubation, as shown in FIG. 2B. The mono-sialylated structures exhibited 3% acid loss and the bi-sialylated structures exhibited 6% sialic acid loss with the overnight incubation.

Combined, these results demonstrate that labeling temperatures and incubation times can be important in reductive amination. For example, though shorter incubation times for APTS labeling may lower signal intensity, FIG. 2B demonstrates that overnight labeling may also generate sialic acid loss. Based on the above findings, the remainder of this exemplary process utilized a labeling incubation time of two hours at 37° C.

To compensate for the lower signal intensity of the shorter incubation, the effect of catalyst concentration (acetic acid) and APTS concentration on the reductive amination reaction was analyzed, as shown in Table 1 (below). Using 20 mM APTS in 15, 20 and 25% acetic acid, mono- and bi-sialylated glycan standards (A2G2S2, A2G2S1, FA2G2S2 and FA2G2S1), were labeled, while trying to avoid any sialylation loss. Examination of the peak area percentages demonstrated that there was no detectable sialic acid loss, while significantly higher peak intensities were obtained, with increased (20%) acetic acid concentration, as shown in Table 1 (Section A).

Figure 2:
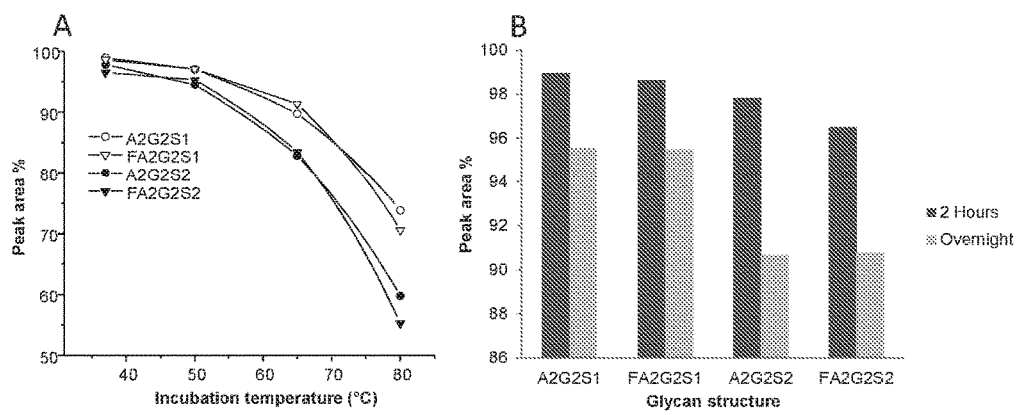
FIGS. 2A-B demonstrate the effect on desialyation of labeling incubation temperature and time in accordance with various aspects of the applicants' teachings.

The effect of various APTS concentrations, in combination with the results of FIG. 2 and Table 1 (Section A), is depicted in Table 1 (Section 2). Maltooligosaccharide ladders were labeled in triplicates using 20, 40 and 80 mM APTS in 20% acetic acid at 37° C. for two hours. As shown in Table 1 (Section B), increasing the APTS concentration increased the labeling efficiency. However, because the exemplary magnetic bead based method described below utilized at least 20 μL of labeling reagents, a higher volume of 40 mM APTS was utilized despite the higher labeling efficiencies demonstrated by the 80 mM APTS.

Utilizing the higher dye and catalyst concentrations, released glycans from 100 μg IgG, fetuin, and RNase B glycoprotein standards were labeled in duplicates using 40 mM APTS in 20% acetic acid at 37° C. for two hours and compared to the original labeling strategy for two hours and overnight (20 mM APTS, 15% acetic acid, FIG. 2B). As shown in Table 1 (Section C), the combination of higher dye and catalyst concentration resulted in ~20% higher labeling efficiency compared to the original two hours labeling without any sialic acid loss, though less than the efficiency of the overnight labeling (in which sialic acid loss was detected). In sum, these results demonstrated that labeling at 37° C. for two hours with 40 mM APTS in 20% acetic acid can effectively increase labeling efficiency, while generating less sialic acid loss.

TABLE 1

Optimization of labeling conditions to increase the labeling efficiency Magnetic bead based sample preparation

| Section A | | | |
|---|---|---|---|
| Acetic acid cc. | 15% | 20% | 25% |
| A2G2S1 | 1.90 | 10.04 | 10.95 |
| A2G2S2 | 1.14 | 5.25 | 5.88 |
| FA2G2S1 | 6.61 | 14.94 | 15.52 |
| FA2G2S2 | 3.20 | 13.04 | 13.52 |
| Section B | | | |
| APTS cc | 20 mM | 40 mM | 80 mM |
| 3 Ladders average | 14.64 | 39.33 | 46.03 |
| SectionC | | | |
| Labeling strategy | 2 H original | 2 H new | OV original |
| IgG | 9.47 | 24.22 | 52.91 |
| fetuin | 18.93 | 28.17 | 66.31 |
| RNase B | 13.16 | 23.50 | 63.34 |

As noted above, the exemplary protocol utilizes magnetic beads for sample preparation to accommodate automation, while avoiding centrifugation steps that make automation difficult.

In this exemplary protocol, carboxyl coated magnetic beads were used to capture complex carbohydrates following their release from the glycoconjugates (i.e., purification after glycan release) and when fluorophore-labeled (i.e., purification after APTS labeling).

In order to clean the APTS reaction mixture (i.e., to remove excess, unconjugated APTS), it was attempted to determine the minimum amount of magnetic bead suspension necessary for obtaining adequate purification, while minimizing any possible sample loss. APTS labeled hIgG (complex type), fetuin (highly sialylated) and RNase B (high mannose type) glycans were purified in triplicates using 200 μL magnetic bead suspension. Binding and washing steps were accomplished by using 150 μL 87.5% acetonitrile, while the elution step was accomplished with the use of 25 μL of water. The more than 150 μL of magnetic bead suspension and binding/elution solutions were readily handled by automatic pipettors, and could likewise be accommodated by simple liquid handling robots using regular pipette tips or syringes. The eluate was directly analyzed by CE-LIF without any further processing. Second and third elution fractions were also analyzed to assess the efficiency of the first elution. It was found that when the clean-up mixture was suspended properly and 25 μL water was used for elution, no detectable sample remained on the beads (i.e., the second and third elution gave negative results). On the other hand, when only 15 μL water was used in the first elution, traces of remaining APTS labeled glycans were detected in the subsequent elutions.

Figure 3:
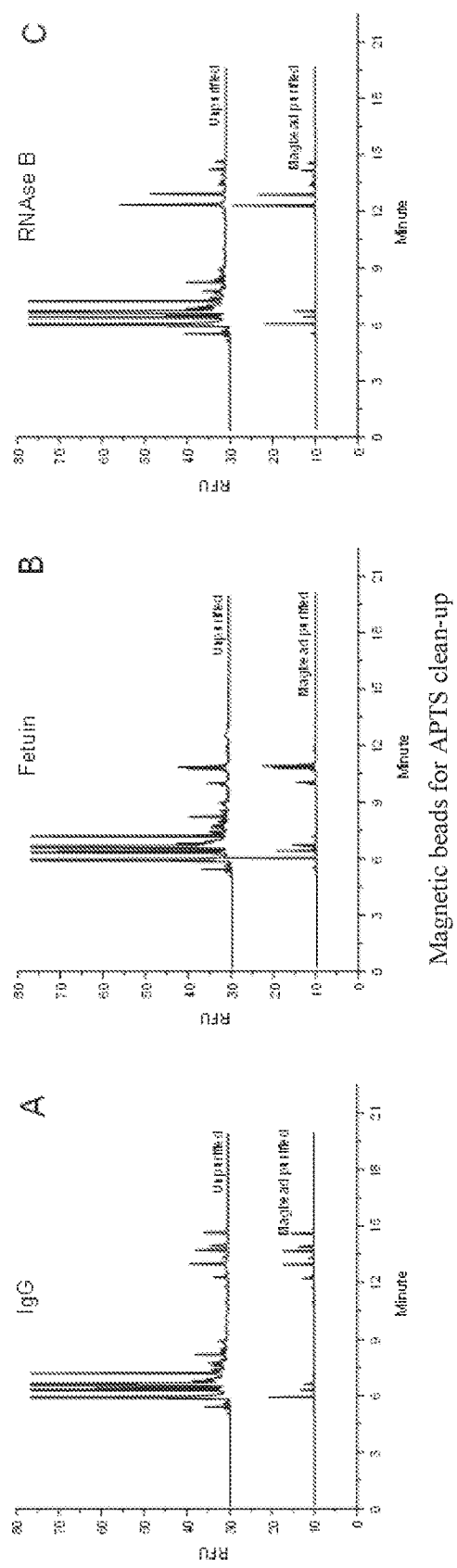
FIGS. 3A-C illustrate an exemplary peak area distribution of various glycan structures using an exemplary magnetic bead based cleanup protocol in accordance with various aspects of the present teachings relative to conventional sample cleanup methods.

Importantly, no differences were observed in peak area distribution using this magnetic bead based cleanup protocol in comparison to conventional sample cleanup methods reported in the literature, suggesting no apparent bias for the different glycan structures (neutral, sialylated, high mannose) towards the beads while most of the free APTS was removed during the clean-up, as shown in FIGS. 3A-C.

A similar approach was utilized to capture the released glycans after PNGase F digestion. Magnetic beads in 87.5% acetonitrile solution were added to the PNGase F reaction mixture after the incubation step to bind the released glycans. In this case, however, the free glycans were eluted by an aqueous APTS solution (40 mM in 20% acetic acid) followed by the addition of the reducing agent (such as 1 M pic-BH$_3$ in MeCN, or NaB$_3$CN in THF) to immediately initiate the labeling reaction without any interim steps. Again, this approach while very effective did not require any vacuum centrifugation based sample pre concentration or any other purification steps to remove the remaining polypeptide chain and PNGase F enzyme in the digestion reaction mixture.

Magnetic Bead Based Sample Preparation Protocol

Figure 4:
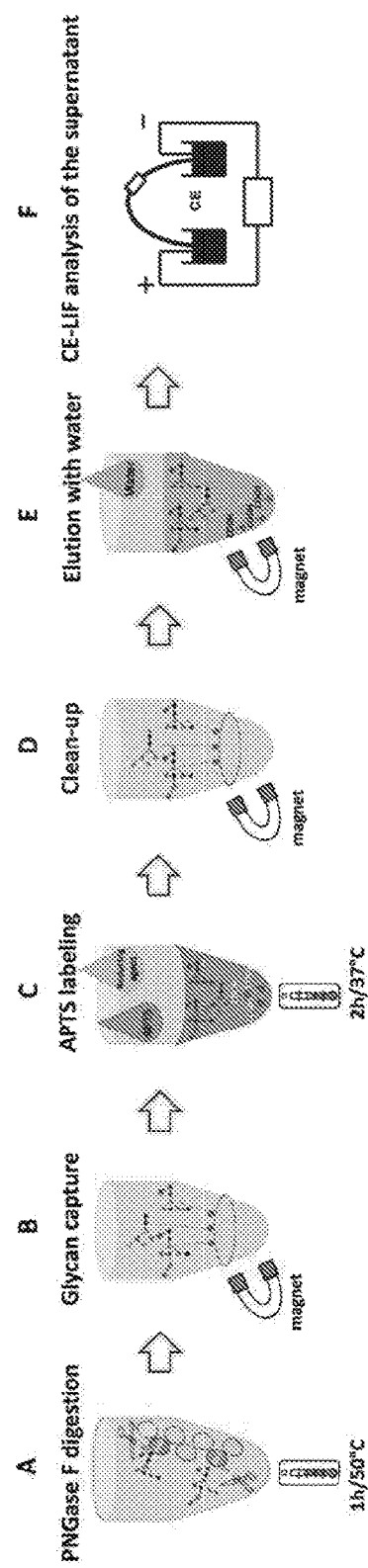
FIG. 4 schematically depicts an exemplary magnetic bead based sample preparation workflow for N-glycosylation analysis in accordance with various aspects of the present teachings.

In accordance with the above optimizations and as schematically depicted in FIG. 4, the following exemplary magnetic bead based glycan sample preparation protocol was performed.

With reference now to FIG. 4, the exemplary magnetic bead based glycan sample preparation protocol began with a one hour PNGase F digestion at 50° C. (Step A). Then, as shown in Step B, the exemplary method utilized a magnetic bead based partitioning of the released glycans from the remaining polypeptide chains and digestion enzyme using 200 μL magnetic bead suspension in 87.5% final acetonitrile concentration. The tube was then placed on the magnet. After removing the supernatant, the captured glycans were eluted from the beads in the same tube by the addition of 21 μL 40 mM APTS in 20% acetic acid, and the reductive amination reaction was started with the addition of 7 μL reducing agent (such as of 1 M pic-BH$_3$ in MeCN or NaB$_3$CN in THF) (Step C). Following a two hour incubation at 37° C., the excess labeling dye was removed in Step D by using the same magnetic beads and approach as in Step B. After pouring off the supernatant, the captured APTS-labeled glycans were eluted from the beads by the addition of 25 μL of HPLC water and partitioned by placing the tube on the magnet (Step E). The eluate/supernatant was removed and analyzed by CE-LIF (Step F).

The reliability and reproducibility of the method was demonstrated by preparing six IgG, fetuin and RNase B samples utilizing the exemplary magnetic bead based protocol and compared to a conventional overnight incubations and centrifugation-based protocol, similar to as described in Varadi, C., et al., *Analysis of haptoglobin N-glycome alterations in inflammatory and malignant lung diseases by capillary electrophoresis*, Electrophoresis., 2013. 34(16): p. 2287-94. Three repetitions were used with each release generating 54 dataset/preparation platforms. All samples were analyzed for representing of neutral and slightly sialylated (Panel A), high mannose (Panel B) and highly sialylated (Panel C) glycans. Mann-Whitney pairwise comparison was used to explore the differences in peak area percentages.

Table 2 demonstrates the efficiency of the optimized processes described above in accordance with various aspects of the present teachings, in that there were no significant differences in the area percentages between the protocols except the higher sialylation level of fetuin using the shorter incubation. Excellent reproducibility was observed by using the full magnetic bead based protocol. Mann-Whitney pairwise comparison was applied to explore the differences in peak area percentages. Integrating 28 peaks, the significance (p) level was examined between the two methods where only 4 peaks showed significant differences ($p<0.05$). All of the different peaks were highly sialylated fetuin glycans and similarly to the previous discussion regarding labeling optimization, the overnight method produced lower sialylation levels suggesting the importance of shorter incubation time during reductive amination. The significantly higher area percentage of peaks 1, 2 generated by the magnetic bead based protocol correlates with the lower values of peaks 5, 7, suggesting that the desialylation of species with high sialylation rate (tetra- and tri-sialylated) increased the amount low sialylated species (bi- and mono-sialylated).

observed at 50° C., though an increase in RFU values was also found, as during digestion optimization. Increased intensity was detected with longer incubation times, with significantly higher intensities at 50° C. At this temperature,

TABLE 2

Measured differences between two methods examining the peak area percentage of 28 N-glycans

| | Magbead protocol Average Area % | STDEV | RSD % | Overnight protocol Average Area % | STDEV | RSD % | Mann-Whitney significance level |
|---|---|---|---|---|---|---|---|
| Panel A IgG | | | | | | | |
| FA2G2S2 | 1.19 | 0.04 | 3.72 | 1.21 | 0.09 | 7.01 | 0.937 |
| FA2BG2S2 | 1.23 | 0.03 | 2.24 | 1.20 | 0.03 | 2.55 | 0.132 |
| FA2(3)G1S1 | 1.71 | 0.06 | 3.78 | 1.73 | 0.10 | 5.77 | 0.818 |
| FA2G2S1 | 7.45 | 0.25 | 3.34 | 7.48 | 0.31 | 4.12 | 0.937 |
| FA2BG2S1 | 1.74 | 0.16 | 8.98 | 1.65 | 0.17 | 10.41 | 0.485 |
| FA2 | 22.12 | 0.47 | 2.11 | 22.23 | 0.15 | 0.68 | 0.699 |
| FA2B | 3.97 | 0.11 | 2.83 | 3.97 | 0.04 | 1.12 | 0.589 |
| FA2(6)G1 | 22.93 | 0.40 | 1.76 | 23.01 | 0.60 | 2.61 | 1.000 |
| FA2(3)G1 | 11.59 | 0.06 | 0.51 | 11.57 | 0.17 | 1.49 | 0.589 |
| FA2B(6)G1 | 4.86 | 0.41 | 8.52 | 4.69 | 0.14 | 3.08 | 0.818 |
| FA2B(3)G1 | 1.02 | 0.09 | 9.12 | 1.07 | 0.06 | 5.39 | 0.132 |
| FA2G2 | 18.13 | 0.47 | 2.61 | 18.30 | 0.12 | 0.64 | 0.589 |
| FA2BG2 | 1.46 | 0.04 | 3.01 | 1.40 | 0.04 | 2.56 | 0.065 |
| Panel B RNaseB | | | | | | | |
| Man5 | 43.45 | 0.62 | 1.43 | 43.90 | 0.37 | 0.85 | 0.132 |
| Man6 | 33.39 | 0.36 | 1.09 | 33.50 | 0.25 | 0.74 | 0.699 |
| Man7* | 3.56 | 0.13 | 3.59 | 3.51 | 0.04 | 1.00 | 0.394 |
| Man7** | 2.58 | 0.08 | 3.17 | 2.52 | 0.07 | 2.69 | 0.240 |
| Man7*** | 2.18 | 0.03 | 1.17 | 2.22 | 0.11 | 5.10 | 0.699 |
| Man8 | 8.60 | 0.30 | 3.51 | 8.22 | 0.13 | 1.63 | 0.065 |
| Man9 | 6.00 | 0.35 | 5.81 | 6.04 | 0.23 | 3.80 | 0.699 |
| Panel C fetuin | | | | | | | |
| Peak 1 | 6.95 | 0.28 | 3.97 | 5.08 | 0.25 | 4.92 | 0.002 |
| Peak 2 | 15.46 | 0.58 | 3.72 | 11.43 | 0.47 | 4.09 | 0.002 |
| Peak 3 | 3.19 | 0.07 | 2.13 | 3.24 | 0.10 | 3.13 | 0.485 |
| Peak 4 | 3.97 | 0.11 | 2.82 | 4.11 | 0.18 | 4.34 | 0.065 |
| Peak 5 | 25.93 | 0.59 | 2.27 | 27.90 | 0.32 | 1.16 | 0.002 |
| Peak 6 | 32.57 | 0.30 | 0.92 | 32.67 | 0.21 | 0.65 | 0.589 |
| Peak 7 | 8.45 | 0.14 | 1.61 | 12.73 | 0.67 | 5.27 | 0.002 |
| Peak 8 | 3.32 | 0.12 | 3.49 | 3.17 | 0.14 | 4.50 | 0.093 |

Example 2

APTS Labeling Optimization

Conditions for labeling so as to achieve the labeling efficiency of conventional centrifugation-based methods with respect to peak intensity and area distribution, while nonetheless accommodating simple liquid handling robots and magnetic bead based automation, were analyzed. In accordance with various aspects of the present teachings, high labeling efficiency was achieved without overnight incubation and vacuum-centrifugation based sample concentration.

Figure 5:
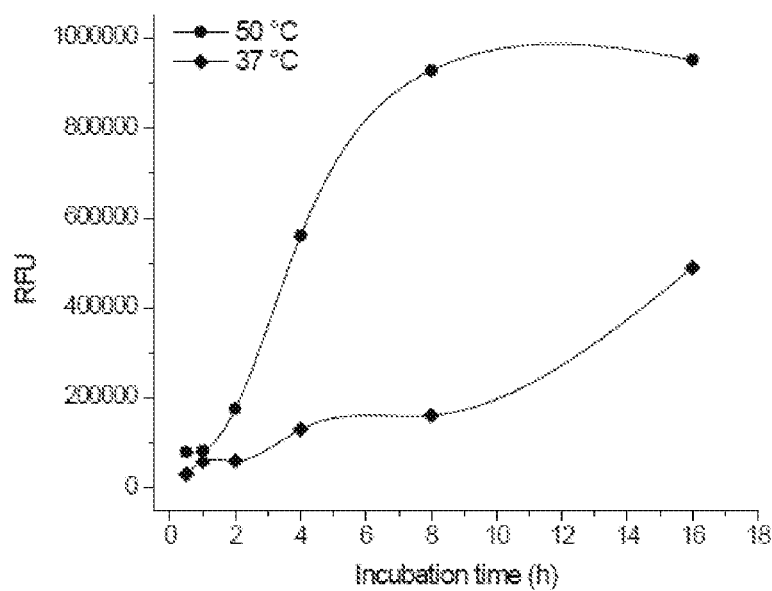
FIG. 5 demonstrates the effect of temperature and incubation time on APTS labeling efficiency in accordance with various aspects of the applicants' teachings.

Incubation conditions for APTS labeling were tested at 37° C. and 50° C. using 0.5, 1, 2, 4, 8 and 16 hour incubation times for glycans released from three IgG samples (100 μg/sample) and three fetuin samples (100 μg/sample). The labeling conditions applied were the same that in previously the published protocols, i.e., 6 μL of 20 mM APTS and 2 μL of 1 M NaBH$_3$CN in THF. As above, three replicates were made with each release generating nine data points per labeling condition. As shown in FIG. 5, an approximately 2% decrease in the peak area of sialyated fetuin glycans was only 4 hours of incubation time gave similar RFU values that of the overnight reaction at 37° C.

Figure 6:
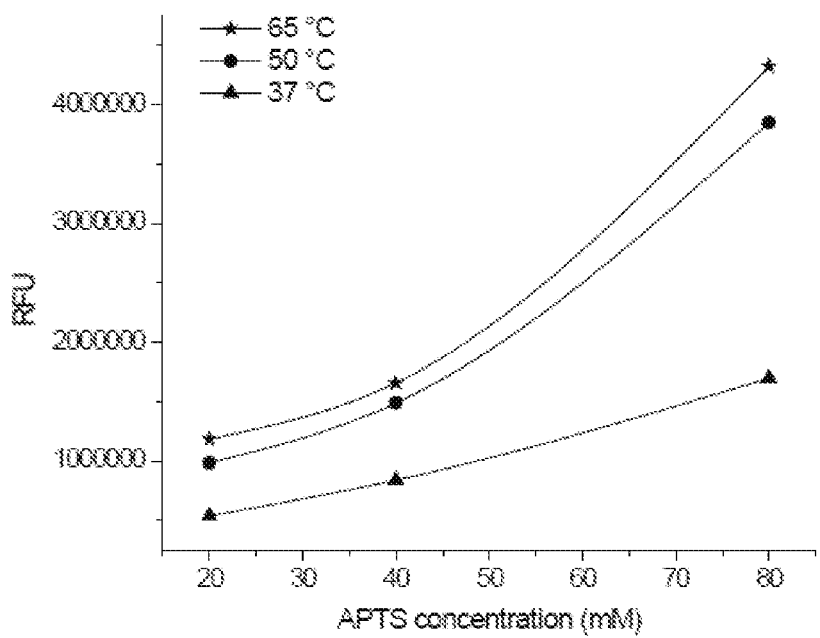
FIG. 6 demonstrates the effect of APTS concentrations on labeling efficiency at various incubation temperatures in accordance with various aspects of the applicants' teachings.

To further decrease derivatization time, the minimum APTS concentration required to still obtain high RFU values in a two hour reaction was determined. Maltooligosaccharide ladder samples were labeled with 20, 40 and 80 mM APTS at 37° C., 50° C., and 65° C. followed by CE-LIF. With reference now to FIG. 6, the effect of labeling temperature is clearly shown as the 37° C. labeling methods revealed a slight increase with elevated APTS concentration, while at 50° C. and 65° C. significantly higher values were detected.

These results demonstrate that labeling temperatures can be crucial in analysis of pharmaindustrially important glycoproteins, such as monoclonal antibodies. For example, though lower incubation temperatures during APTS labeling may lower RFU values, the reduction in desialylation can help preserve the sialylated glycans. Based on the above findings, the remainder of this exemplary process utilized a labeling incubation temperature of 37° C.

Magnetic Bead Based Sample Preparation for Liquid Handling Robots

In order to optimize the glycan sample preparation for easy automation, centrifugation steps, including vacuum centrifugation, were avoided. Rather, as discussed otherwise herein, applicants discovered that carboxyl-coated magnetic beads could be effective in capturing both the released and labeled glycans. The exemplary APTS clean-up protocol was optimized to provide for sufficient magnetic beads, while minimizing sample loss. APTS-labeled fetuin and IgG glycans were purified using 5, 10, 20, 40, 80, 160, and 200 µL magnetic beads in triplicates. Besides the easy handling of magnetic bead based sample preparation, one of the other advantages of the use of magnetic beads is their applicability in small volumes, e.g., 20 µL. Binding and washing steps were made with 150 µL 87.5% acetonitrile, while the elution step only utilized 25 µL of water, which was then directly analyzed by CE-LIF. Second and third elution fractions were also evaluated to determine the efficiency of the first elution. It was determined that when the first elution was made in 25 µL and suspended properly, no sample remained on the beads, i.e., the second and third elutions were negative. However, when the first elution was made in only 15 µL some remaining sample was detected.

Figure 7:
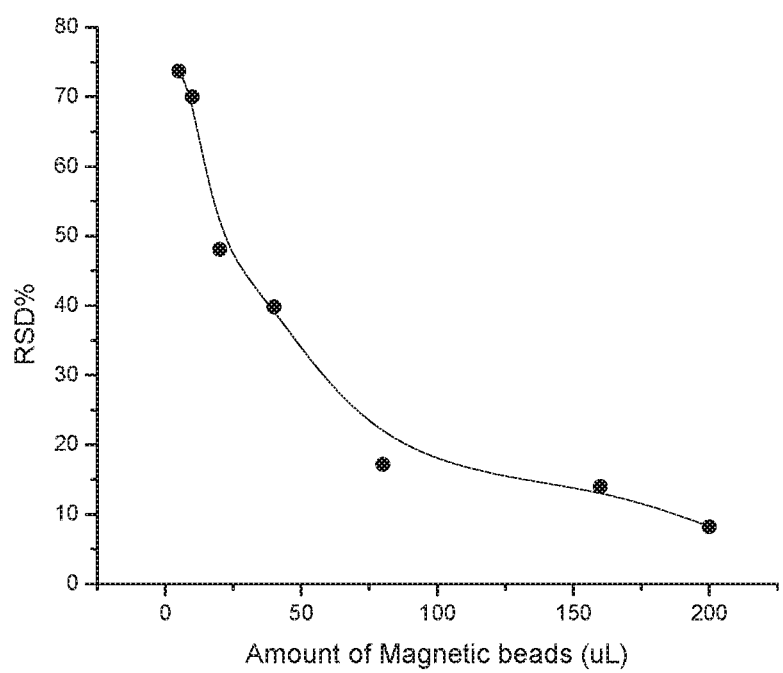
FIG. 7 demonstrates the reproducibility as the function of the amount of magnetic bead suspension used in accordance with various aspects of the applicants' teachings.

No differences were found in peak area distribution using the magnetic bead based cleanup protocol, proving no particular bias for the different glycans towards the beads. However, as shown in FIG. 7, significant differences were observed in the reproducibility of the cleaned-up samples based on the amount of magnetic beads. RSD % of RFU values were calculated from triplicate magnetic bead based clean up steps, revealing the highest reproducibility with the use of 200 µL of magnetic beads.

The same magnetic bead based approach was likewise used for glycan capture following the PNGase F digestion step. After the one hour PNGase F digestion step, 113 µL acetonitrile was added to the reaction mixture (final concentration 87.5%). After one washing step with 87.5% acetonitrile, the glycans were eluted by 21 µL 40 mM APTS in 20% aqueous solution of acetic acid. The addition of the reducing agent initiated the labeling reaction without the need for centrifugation based sample concentration.

Magnetic Bead Based Sample Preparation Protocol

As schematically depicted in FIG. 8, the following exemplary magnetic bead based glycan sample preparation protocol was performed. The exemplary magnetic bead based glycan sample preparation protocol began with a one hour PNGase F digestion at 50° C., and the released glycans were captured by adding acetonitrile to the reaction mixture (final concentration 87.5%) so as to associate the released glycans with the magnetic beads. The beads were drawn down by a magnet and the supernatant removed. The glycans were eluted by 21 µL 40 mM APTS in a 20% aqueous solution of acetic acid. The APTS labeling reaction was initiated with the addition of 7 µL of the reducing agent (1 M NaBH$_3$CN in THF) and incubated at 37° C. for two hours. 150 µL acetonitrile (final concentration of 87.5%) was again added to capture with the magnetic beads the labeled glycans. The supernatant was removed and the beads and glycans were twice washed with the acetonitrile (150 µL, final concentration of 87.5%). 25 µL of HPLC water was then added to elute the labeled glycans and the eluate containing the labeled glycans was subjected to CE-LIF.

The above data demonstrates that when compared to conventional glycan sample preparation protocols utilizing overnight, centrifugation-based digestion/labeling, processes in accordance with the present teachings can provide comparable results in approximately four hours. Moreover, without the need of any centrifugation and or vacuum centrifugation steps as in conventional methods, full automation can be enabled with simple liquid handling robots for high throughput sample processing, for example, in a 96-well plate with excellent yield, and high reproducibility.

Automated Magnetic Bead Based Sample Preparation

The sample preparation method in the within teachings was utilized in a fully automated protocol which included endoglycosidase digestion, rapid fluorophore labeling and clean-up in a high throughput sample processing system. A liquid handling robot (Biomek FX$^P$ Laboratory Automation Workstation, Beckman Coulter, Brea, Calif.) was utilized together with a Capillary Electropheresis-Lased Induced Fluorescence (CE-LIF) device (PA 800 plus, Beckman Coulter, sold through Sciex, Brea, Calif.).

The automation workstation was setup with 96 well plate holders, a magnetic stand, 1000 µL and 25 µL pipette tips, a quarter reservoir, and sample and reagent vials. The quarter reservoir contained acetonitrile (Sigma Aldrich, MO) and the Agencourt CleanSeq magnetic beads (Beckman Coulter, Brea, Calif.). The reagent vials contained reagents for the PNGase F digestion (Prozyme, CA), 8-aminopyrene-1,3,6-trisulfonate (ATPS) (Beckman Coulter, sold through Sciex, Brea, Calif.) in 20% acetic acid and 1 M sodium-cyanoborohydrate (in THF). To reduce evaporation induced volume loss, a pipette box lid was used to cover the quarter reservoirs. The glycoprotein samples were incubated in a Biomek vortex heater block. For better re-suspension, an extra plate was applied under the sample plate, in which case the magnets were positioned under the sample plate, rather than off to the side. In this way the magnet could pull down the magnetic beads to the bottom of the vials and with fast aspiration/dispensing, the beads were easily re-suspendable.

The enzymatic digestion using PNGase F was performed at 50° C. for 1 hour followed by glycan capture on the magnetic beads in 87.5% acetonitrile medium. APTS labeling of the bound carbohydrates was initiated in situ on the beads by the addition of sodium cyanoborohydride and incubated at 37° C. for 2 hours. After the enzymatic digestion, the glycans are recaptured by the addition of 100% acetonitrile resulting in a 87.5% concentration regarding the acetonitrile. The APTS labeling reaction is started in situ on the beads at 37° C. for 2 hours by the addition of 21 µl of 40 mM APTS in 20% acetic acid and 7 µl of 1 M sodium cyanoborohydride in THF. Next, the labeled glycans are recaptured again on the beads by the addition of 100% acetonitrile to reach the final concentration of 87.5%. Then, the beads are washed repeatedly with 87.5% acetonitrile media for high efficiency dye removal. The fluorophore labeled glycans were eluted from the beads by the addition of 25 µL of water and were ready for CE-LIF (488 nm excitation, 520 nm emission). For the separation, 20 cm effective length NCHO capillaries (Beckman Coulter sold through Sciex) were used (30 cm total length, 50 µm ID) with 25 mM lithium acetate (pH 4.75) background electrolyte containing 1% polyethylene oxide (Mv~900,000, Sigma-Aldrich). The applied voltage was 30 kV and the separation temperature was 20° C. The samples were pressure injected by 3 psi for 6 seconds. This composition was found to allow rapid separation of glycans in a short period of time. The entire liquid handling protocol was programmed using the Biomek Software version 4.0. The CE-LIF data were acquired and analyzed by the Karat 32 software package (Beckman Coulter, sold through Sciex, Brea, Calif.).

The laboratory automation workstation offered fast sample preparation option, reduced flow-induced shear strain on native biological sample matrices and minimized contamination risks. For higher accuracy liquid handling or unknown source and amount of samples conductive pipette tips can be used that are capable of high precision liquid handling. Due to the large amount of deck space available in the liquid handling system, buffer preparation for the CE-LIF analysis was also done automatically including the solubilization step of the separation sieving matrix.

Figure 9:
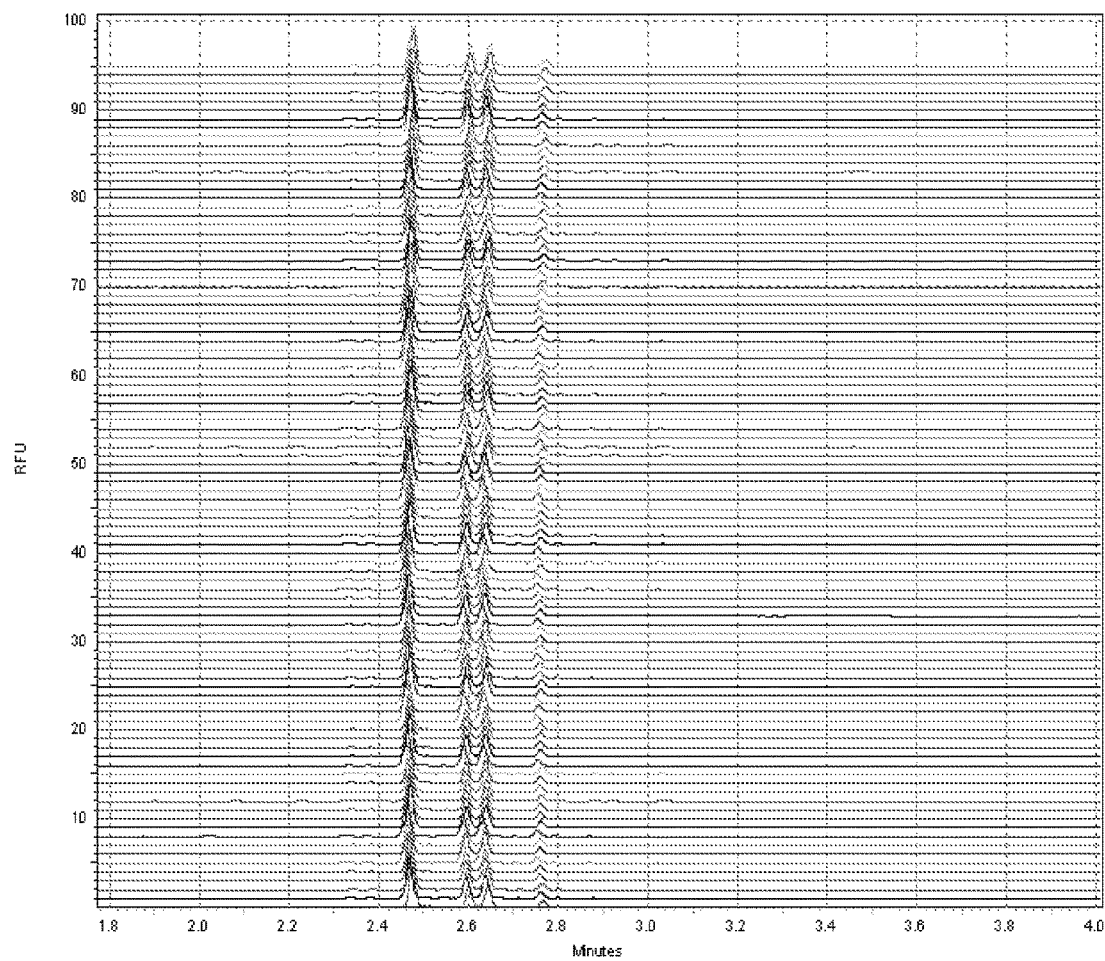
FIG. 9 shows the results obtained from CE-LIF analysis of multiple APTS labeled IgG glycans utilizing an automated liquid handling device in accordance with various aspects of the present teachings.

The resulting fluorophore labeled glycans were subject to CE-LIF analysis that was optimized for rapid separation to accommodate the high throughput of the fully automated preparation process. The electropherograms of the APTS labeled IgG glycans, injected consecutively from the 96 well plate coming out of the liquid handling robot, are shown in FIG. 9. The baseline separation of the major IgG glycans were obtained in less than 3 minutes. This separation method can be readily applied for large scale processes where rapid analysis of hundreds of samples is crucial, such as in clone selection.

More particular procedures concerning the automated method are discussed herein.

200 μl of Agencourt Cleanseq magnetic beads are added from the quarter reservoir to the sample plate after quick aspiration and dispensing for bead re-suspension. In general, the addition of the magnetic particles is at the dye (label) removal step at the second part of the process, but, adding the beads at the first step enables the usage of all 96 well of the plates for samples—there is no need for separate wells for sample and bead preparations. From this step to the dye (label) cleaning step, the beads are constantly kept on the wall by the magnetic stand. It has been found that using this can lead to improved results due the reduction in bead loss.

After 30 sec of waiting, the supernatant (storage solution) is removed. The removal of the liquids is always performed from the bottom of the wells with low aspiration speed. In this case, those magnetic beads that the magnet could not pull down during initial draw down can be caught, while the liquid level is lowering.

20 μL of glycoprotein sample per well is added from the sample rack or reservoir to the sample plate (for a 96 well plate, approximately 960 μL total of sample). Using this amount of sample is enough to cover the beads with liquid preventing the beads from drying out.

1 μL of denaturation buffer (NEB 10× Denaturating buffer) is added per sample from the regent rack to the sample plate (for a 96 well plate, approximately, 96 μL total of buffer). Each sample is incubated at 65° C. for 10 minutes on the vortex shaker (1000 rpm).

In parallel with the 10 minute incubation step, 2.5 μL of NP-40 (NEB 10% NP-40), 2.5 μL of reaction buffer (NEB 10× G7 Reaction buffer), 3 μL of water and 1 μL of PNgase F enzyme (NEB) are mixed per sample on the reagent plate or reservoir (for a 96 well plate, approximately 240 μL total of NP-40 and reaction buffer, approx. 96 μL total of PNgase F enzyme and approx. 288 μL of water). This is now the digestion mixture. Mixing reagents for enzymatic digestion in parallel to the incubation step allows for a decrease in the time between sample preparation steps. The temperature is lowered on the thermostat to 50° C.

19 μL of digestion mixture is added to each well (for a 96 well plate, approx. 1824 μL total of digestion mixture)—total sample volume is 30 μL. This solution addition is performed on the vortex—no labware movement is needed.

Sample is incubated at 50° C. for 60 minutes on the vortex shaker (1000 rpm).

210 μL of 100% acetonitrile per sample is added to obtain the 87.5% acetonitrile final concentration (for a 96 well plate, approximately 20.16 mL total of acetonitrile). This solution addition is performed on the vortex unit to prevent the beads from strongly sticking to the wall of the wells due to the magnet. During the addition, a different pipetting technique is used. Due to acetonitrile spilling out from the pipette tips, additional air is aspirated after the solution. When dispensing, the air is pushed out above the sample level, then the acetonitrile is dispensed while the tips are moved up. Using this pipetting technique is enough to mix the organic solution in the aqueous sample without making separate layers.

The sample is vortexed for 20 seconds at 1600 rpm at room temperature (25° C.).

Material is incubated at room temperature (25° C.) for 2 minutes and 40 seconds to allow glycan re-capture (total glycan capture time is 3 minutes). In parallel with the 3 minutes glycan capture step, 7 μL of 1 M sodium-cyanoborohydrate in THF and 21 μl of 20 mM APTS mixed on the reagent plate or reservoir (for a 96 well plate, approximately 672 μL total of 1 M sodium-cyanoborohydrate and 2.016 mL of 20 mM APTS). This is now the dying/labeling solution.

The sample plate is put back on to the magnetic stand. After 30 seconds pause, while the beads are being captured with the magnets, the supernatant is removed. After supernatant removal, 28 μL of labeling dye solution is added per well (for a 96 well plate, approximately 2.668 mL total of dying solution). Material is incubation at 37° C. for 2 hours on the vortex shaker (1000 rpm).

196 μL of 100% acetonitrile is added per sample (for a 96 well plate, approximately 18.816 mL of acetonitrile) on the vortex unit to re-bond the glycans to the beads. The sample is vortexed for 20 seconds at 1600 rpm at room temperature (25° C.) and sample is then allowed to incubate at room temperature (25° C.) for 2 minutes and 40 seconds for glycan capture (total glycan capture time is 3 minutes).

The sample plate is put back on to the magnetic stand. After 30 seconds pause to allow the beads to be captured with the magnets, the supernatant is removed.

While the glycan capture can be performed by keeping the magnetic beads constantly on the wall, using a similar principle as in the dye cleaning step, the efficiency can be low. Therefore, the re-suspension of the beads is preferred. In organic media, when acetonitrile is used the beads exhibit strong attraction to the wall of the wells and it is difficult to remove these beads even with hard vortexing. Also, the beads are washed with 87.5% acetonitrile repeatedly, but due to rapid acetonitrile evaporation, this results in a concentration that changes with time.

To obtain good re-suspension, and avoid concentration changes the following procedure can be utilized, repeated 3 times.
  a. Addition of 20 μl of water. In aqueous solutions, the CleanSeq beads are less likely bond to the wall, and can be re-suspended easily by a simple vortexing step.
  b. Vortexing the sample for 10 seconds at 1600 rpm at room temperature (25° C.).
  c. Addition of 140 μl of 100% acetonitrile. In this case only 100% acetonitrile is used during the protocol, so, even if it is evaporating, the concentration remains the same.
  d. Vortexing the sample for 20 seconds at 1600 rpm at room temperature (25° C.).
  e. Incubation at room temperature (25° C.) for 2 minutes and 40 seconds for glycan re-capture (total glycan capture time is 2 minutes).
  f. The sample plate is put back on to the magnetic stand.
  g. After 30 seconds pause, while the beads are being captured by the magnets, the supernatant is removed.

Elution of the samples with 20 μl of water by vortexing it for 30 seconds at 1600 rpm, then the sample plate is put back on the magnetic stand, and after 30 sounds, the samples are transferred to a universal vial, ready to be analyzed using capillary electrophoresis.

Figure 10:
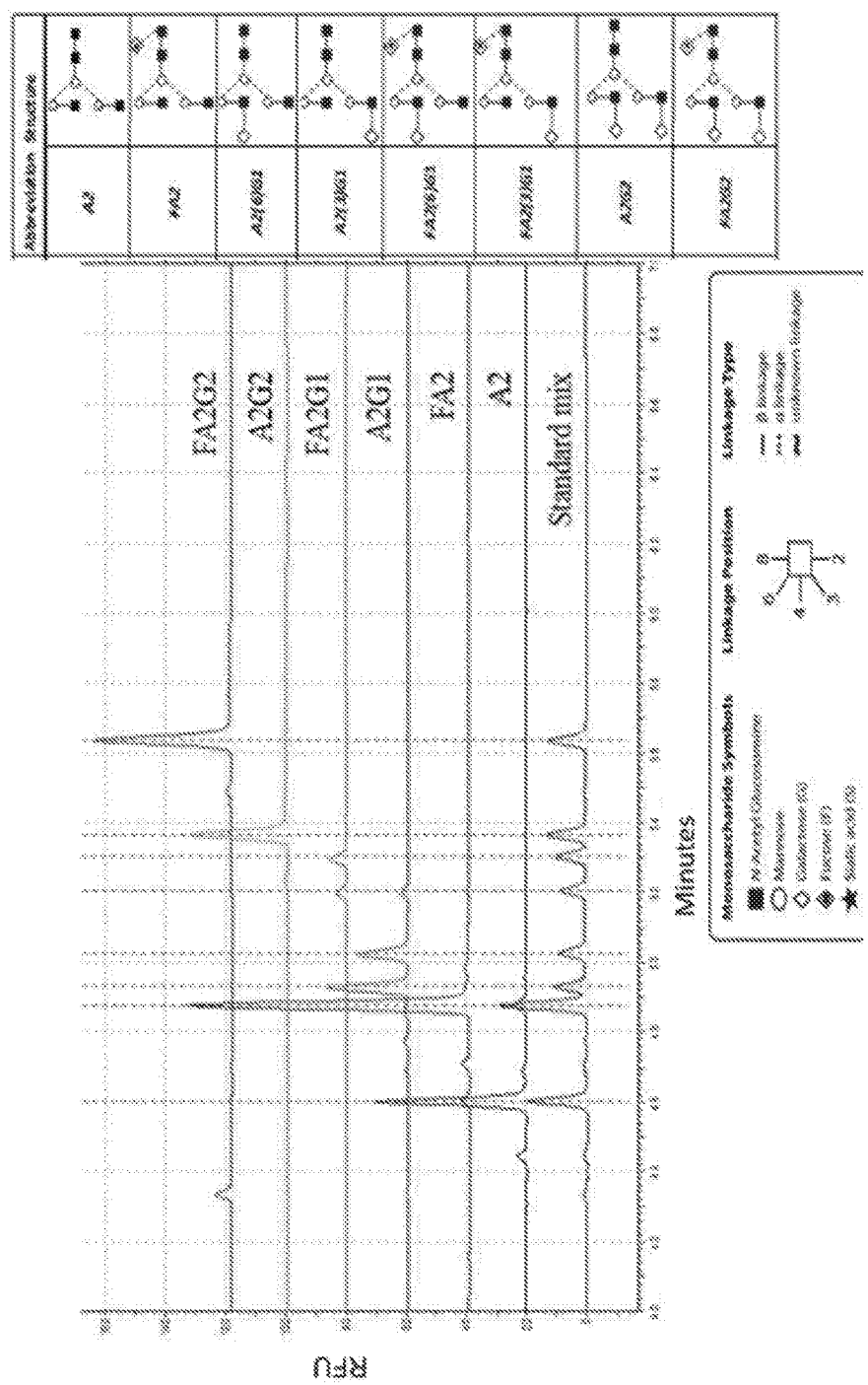
FIG. 10 shows results from a CE-LIF analysis of individual glycans and a mixture of glycans in accordance with various aspects of the present teachings.

An analysis of individual glycans (FA2G2, A2G2, FA2G1, A2G1, FA2 and A2) as well as mixture of the individual glycans was accomplished using CE-LIF using the within teachings. Separation using CE was performed with a gel composition containing lithium acetate buffer with concentration of 30 mM, at pH of 4.75, polyethylene oxide ($M_v$ of about 900 kDa) at concentration of 1%, ethylene glycol at concentration of about 20% and linear polyacrylamide (MW of about 10 kDa) at concentration of about 3%. Results of the analysis are shown in FIG. 10.

REFERENCES

All references listed herein are incorporated by reference in their entirety.
1. Bogyo, M. and P. M. Rudd, New technologies and their impact on 'omics' research. Curr Opin Chem Biol., 2013. 17(1): p. 1-3. doi: 10.1016/j.cbpa.2013.01.005.
2. Maeda, E., et al., Analysis of Nonhuman N-Glycans as the Minor Constituents in Recombinant Monoclonal Antibody Pharmaceuticals. Analytical Chemistry (Washington, D.C., United States), 2012. 84(5): p. 2373-2379.
3. Ma, S. and W. Nashabeh, Carbohydrate Analysis of a Chimeric Recombinant Monoclonal Antibody by Capillary Electrophoresis with Laser-Induced Fluorescence Detection. Analytical Chemistry (Washington, D.C., United States), 1999. 71(22): p. 5185-5192.
4. Royle, L., et al., HPLC-based analysis of serum N-glycans on a 96-well plate platform with dedicated database software. Analytical Biochemistry, 2008. 376(1): p. 1-12.
5. Evangelista, R. A., A. Guttman, and F.-T. A. Chen, Acid-catalyzed reductive amination of aldoses with 8-aminopyrene-1,3,6-trisulfonate. Electrophoresis, 1996. 17(2): p. 347-51.
6. Olajos, M., et al., Sample Preparation for the Analysis of Complex Carbohydrates by Multicapillary Gel Electrophoresis with Light-Emitting Diode Induced Fluorescence Detection. Analytical Chemistry (Washington, D.C., United States), 2008. 80(11): p. 4241-4246.
7. Tarentino, A. L., C. M. Gomez, and T. H. Plummer, Deglycosylation of asparagine-linked glycans by peptide: N-glycosidase F. Biochemistry, 1985. 24(17): p. 4665-4671.
8. Zhou, H., et al., PNGase F catalyzes de-N-glycosylation in a domestic microwave. Analytical Biochemistry, 2012. 427(1): p. 33-35.
9. Szabo, Z., A. Guttman, and B. L. Karger, Rapid Release of N-Linked Glycans from Glycoproteins by Pressure-Cycling Technology. Analytical Chemistry (Washington, D.C., United States), 2010. 82(6): p. 2588-2593.
10. Palm, A. K. and M. V. Novotny, A monolithic PNGase F enzyme microreactor enabling glycan mass mapping of glycoproteins by mass spectrometry. Rapid Commun Mass Spectrom., 2005. 19(12): p. 1730-8.
11. Sandoval, W. N., et al., Rapid removal of N-linked oligosaccharides using microwave assisted enzyme catalyzed deglycosylation. International Journal of Mass Spectrometry, 2007. 259(1-3): p. 117-123.
12. Guttman, A., et al., High-resolution capillary gel electrophoresis of reducing oligosaccharides labeled with 1-aminopyrene-3,6,8-trisulfonate. Anal Biochem., 1996. 233(2): p. 234-42.
13. Guttman, A., F.-T. A. Chen, and R. A. Evangelista, Separation of 1-aminopyrene-3,6,8-trisulfonate-labeled asparagine-linked fetuin glycans by capillary gel electrophoresis. Electrophoresis, 1996. 17(2): p. 412-17.
14. Guttman, A. and T. Pritchett, Capillary gel electrophoresis separation of high-mannose type oligosaccharides derivatized by 1-aminopyrene-3,6,8-trisulfonic acid. Electrophoresis, 1995. 16(10): p. 1906-11.
15. Ruhaak, L. R., et al., Optimized Workflow for Preparation of APTS-Labeled N-Glycans Allowing High-Throughput Analysis of Human Plasma Glycomes using 48-Channel Multiplexed CGE-LIF. Journal of Proteome Research, 2010. 9(12): p. 6655-6664.
16. Ruhaak, L. R., et al., 2-picoline-borane: a non-toxic reducing agent for oligosaccharide labeling by reductive amination. Proteomics., 2010. 10(12): p. 2330-6.
17. Szabo, Z., et al., Improved sample preparation method for glycan analysis of glycoproteins by CE-LIF and CE-MS. Electrophoresis, 2010. 31(8): p. 1389-1395.
18. Su, Y. H., et al., Removal of high-molecular-weight DNA by carboxylated magnetic beads enhances the detection of mutated K-ras DNA in urine. Ann N Y Acad Sci., 2008. 1137:82-91.
19. Vila, A. M., et al., Development of a new magnetic beads-based immunoprecipitation strategy for proteomics analysis. J Proteomics., 2010. 73(8): p. 1491-501.
20. Xu, Y., et al., Solid-Phase Reversible Immobilization in Microfluidic Chips for the Purification of Dye-Labeled DNA Sequencing Fragments. Analytical Chemistry, 2003. 75(13): p. 2975-2984.
21. Bergemann, C., et al., Magnetic ion-exchange nano- and microparticles for medical, biochemical and molecular biological applications. Journal of Magnetism and Magnetic Materials, 1999. 194(1-3): p. 45-52.
22. Yeh, C. H., et al., Magnetic bead-based hydrophilic interaction liquid chromatography for glycopeptide enrichments. J Chromatogr A., 2012. 1224:70-8.
23. Loo, D., A. Jones, and M. M. Hill, Lectin magnetic bead array for biomarker discovery. J Proteome Res., 2010. 9(10): p. 5496-500.
24. Varadi, C., et al., Analysis of haptoglobin N-glycome alterations in inflammatory and malignant lung diseases by capillary electrophoresis. Electrophoresis., 2013. 34(16): p. 2287-94.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

What is claimed is:

1. A method of analyzing one or more glycoconjugates, comprising:
  reacting a sample containing one or more glycoconjugates with a deglycosylation reagent to release glycans from the glycoconjugates;
  associating the glycans with a plurality of magnetic particles;
  applying a magnetic field to draw down the plurality of magnetic particles having the glycans associated therewith;
  removing a supernatant from the drawn-down magnetic particles so as to remove the deglycosylation reagent and deglycosylated sample;
  reacting the glycans with a labeling reagent so as to form labeled glycans;
  analyzing the labeled glycans;

wherein the magnetic particles are carboxyl-coated magnetic beads; and wherein the glycans are associated with the plurality of magnetic particles by adding acetonitrile.

2. The method of claim 1, wherein the one of more glycoconjugates comprises a glycoprotein or glycopeptide.

3. The method of claim 2 wherein the glycoprotein or glycopeptide is an antibody.

4. The method of claim 1, further comprising eluting the glycans from the plurality of magnetic particles prior to reacting the glycans with the labeling reagent.

5. The method of claim 4, wherein the glycans are eluted from the plurality of magnetic particles by adding a mixture comprising the labeling reagent and an acid catalyst.

6. The method of claim 5 wherein the acid catalyst is acetic acid.

7. The method of claim 4, wherein reacting the glycans with the labeling reagent so as to form labeled glycans comprises adding a reducing agent to initiate the reaction of the glycans with the labeling reagent.

8. The method of claim 1, further comprising purifying the labeled glycans.

9. The method of claim 8, further comprising:

associating the labeled glycans with the plurality of magnetic particles;

applying a magnetic field to draw down the plurality of magnetic particles having the labeled glycans associated therewith;

removing a supernatant from the drawn-down plurality of magnetic particles having the labeled glycans associated therewith so to remove excess labeling reagent; and eluting the labeled glycans from the plurality of magnetic particles.

10. The method of claim 9, wherein the labeled glycans are eluted from the plurality of magnetic particles by adding aqueous media.

11. The method of claim 10 wherein the aqueous media is water.

12. The method of claim 1, wherein the labeled glycans are analyzed by capillary electrophoresis, capillary electrophoresis with fluorescent detection, liquid chromatography, liquid chromatography with fluorescent detection, mass spectrometry (MS) or nuclear magnetic resonance (NMR).

13. The method of claim 1, wherein the labeling reagent comprises one of 1-aminopyrene-3,6,8-trisulfonic acid (APTS), 8-aminonaphthalene-1,3,6-trisulfonic acid (ANTS), 2-aminobenzoic acid (2-AB) and 2-anthranilic acid (2-AA).

14. The method of claim 1, wherein reacting the glycans with a labeling reagent further comprises adding a reducing agent.

15. The method of claim 14 wherein the reducing agent comprises $NaBH_3CN$.

* * * * *